(12) United States Patent
Martin (10) Patent No.: US 8,796,629 B2
(45) Date of Patent: Aug. 5, 2014

(54) MEASURING CELL ADAPTED TO SPECTRAL ANALYSIS

(75) Inventor: Hans Göran Evald Martin, Delsbo (SE)

(73) Assignee: Senseair AB, Delsbo (SE)

( * ) Notice: Subject to any disclaimer, the term of this patent is extended or adjusted under 35 U.S.C. 154(b) by 143 days.

(21) Appl. No.: 13/497,382

(22) PCT Filed: Oct. 26, 2010

(86) PCT No.: PCT/SE2010/051153
§ 371 (c)(1),
(2), (4) Date: Mar. 21, 2012

(87) PCT Pub. No.: WO2011/053230
PCT Pub. Date: May 5, 2011

(65) Prior Publication Data
US 2012/0199744 A1    Aug. 9, 2012

(30) Foreign Application Priority Data
Oct. 26, 2009    (SE) ...................................... 0901378

(51) Int. Cl.
*G01J 5/02*    (2006.01)
(52) U.S. Cl.
USPC ........................................................ 250/343
(58) Field of Classification Search
USPC ........................................................ 250/343
See application file for complete search history.

(56) References Cited

U.S. PATENT DOCUMENTS 8,003,945 B1 *   8/2011   Wong .......................... 250/343
8,193,502 B2 *   6/2012   Hodgkinson et al. ..... 250/339.12

(Continued)

FOREIGN PATENT DOCUMENTS

DE    103 03 263    8/2004
GB    2 392 721     3/2004

(Continued)

OTHER PUBLICATIONS

International Search Report issued on Dec. 17, 2010 in International Application No. PCT/SE2010/051153 filed Oct. 26, 2010.

*Primary Examiner* — Christine Sung
(74) *Attorney, Agent, or Firm* — Drinker Biddle & Reath LLP (57) ABSTRACT

A measuring cell adapted for a spectral analysis of a gas sample, where this measuring cell is designed and adapted to co-ordinate, from an IR generating element, emitted converging and/or diverging light beams in a direction toward an IR receiving element, by a plurality of reflections of emitted light beams from a number of reflection surfaces assigned to the inner cavity of the measuring cell, thereby creating a predetermined measuring distance in the inner cavity of the measuring cell, from the IR generating element to the IR receiving element. The cavity of the measuring cell is adapted to contain the gas sample intended for a spectroanalytical absorption measurement. Light beams from the IR generating element are, via a reflection surface, convergingly directed to and/or adapted, such as reflectable, in a first reflection surface in order to, when reflected, via a first focal point, as diverging light beams become directed to a second reflection surface, shaped as a concave reflection surface, as well as via third and fourth reflection surfaces become converging to a focal point, in or in the vicinity of the IR receiving element, in order to form a compact measuring cell.

22 Claims, 3 Drawing Sheets

(56) References Cited

U.S. PATENT DOCUMENTS

| | | |
|---|---|---|
| 2002/0105650 A1 | 8/2002 | Stuttard |
| 2006/0226367 A1 | 10/2006 | Hopkins et al. |
| 2007/0102639 A1 | 5/2007 | Cutler et al. |
| 2007/0114421 A1 * | 5/2007 | Maehlich et al. ............. 250/343 |
| 2008/0239322 A1 | 10/2008 | Hodgkinson et al. |
| 2008/0308733 A1 * | 12/2008 | Doncaster .................... 250/343 |

| | | |
|---|---|---|
| 2009/0135415 A1 | 5/2009 | Park |

FOREIGN PATENT DOCUMENTS

| | | |
|---|---|---|
| SU | 1080076 | 3/1984 |
| WO | 97/18460 | 5/1997 |
| WO | 98/09152 | 3/1998 |
| WO | 2004/063725 | 7/2004 |

* cited by examiner

MEASURING CELL ADAPTED TO SPECTRAL ANALYSIS

CROSS REFERENCE TO RELATED APPLICATIONS

This application is a National Stage of International Application No. PCT/SE2010/051153 filed Oct. 26, 2010, and which claims benefit of Swedish Patent Application No. 0901378-0 filed Oct. 26, 2009, both of which are herein incorporated by reference in their entirety.

TECHNICAL FIELD OF THE INVENTION

The present invention relates generally to a measuring cell, and particularly to a measuring cell adapted to a spectral analysis of a gas sample.

Measuring cells of the relevant kind are designed and adapted to co-ordinate light beams emitted from a means generating light, such as an IR light, in a direction toward a means receiving the light, such as the IR light.

Even if the present invention is based on and provides a general design of a measuring cell, it should be taken into consideration that such a measuring cell may come to use for any electromagnetic radiation, the subsequent description though will be concentrated on a utilization of an IR light (a light falling within the infrared frequency range) and particularly an IR light that affords pulsed light beams over time.

The co-ordination provided here, between the means generating light and the means receiving light, is carried out according to the provisions of the invention, by a utilization of a plurality of reflections of the emitted light beam(s) from and between a number of reflection surfaces and/or simplified reflection points assigned to the inner cavity of the measuring cell.

Since the light beams occur as diverging or converging light rays, these will be reflected in formed reflection surfaces while a central light ray assigned to the light rays will be regarded as reflected in a reflection point.

The opposed placement of the reflection surfaces in the cavity and the shapes of the reflection surfaces, such as plane or curved, thereby provide a predetermined measuring distance in the inner cavity of the measuring cell, where the length of the measuring distance should be extendable through a gas sample and usually be measured from the means generating light to the means receiving light.

The cavity of said measuring cell is adapted to be able to contain the gas sample intended for a spectroanalytical absorption measurement and where this analysis is carried out by a particularly formed electronics, co-ordinated with a calculation circuit including algorithms, which, however, is not described in more detail in the following as its design can be considered to be well known to those skilled in the art.

The inner cavity of the measuring cell and its assigned volume are limited by a first part, such as a bottom part, allocated to the measuring cell in close co-operation with a second part, such as an upper part, allocated to the measuring cell, and where an inlet to and an outlet from the cavity should be assigned to the contained and exchangeable gas sample.

The first part and/or the second part should be assigned recesses and/or seats for supporting the requisite means transmitting and receiving light.

In that connection, assigned recesses are adapted to allow a passage of light beams, generated by the means generating light, and to a passage through the cavity of the measuring cell and assigned a direction toward the means receiving light.

In that connection, assigned seats are adapted to be able to clamp the means generating light and/or the means receiving light to the first and/or second parts of the measuring cell.

Here, light beams, from the means generating light, are directed to and/or adapted, such as reflectable, in a first reflection surface, in order to, when reflected therein, become directed to a second reflection surface, here shaped as a concave reflection surface.

The generated light beams may, on one hand, be generated as a continuously generated light, but the invention gets a special application for light beams that are pulsed over time, foremost in view of the reduction of the heat energy attributed to short and pulsed IR light beams.

The present invention intends to allow reducing the outer volume of the measuring cell, but still be able to afford a relatively long measuring distance, where a ratio "the length of the measuring distance/the outer (inner) volume of the measuring cell" should be kept within selected limits.

BACKGROUND OF THE INVENTION

Methods, arrangements and designs related to the above-mentioned technical field and nature are previously known in a plurality of different embodiments.

As a first example of the background art and technical field to which the invention relates, a measuring cell may be mentioned being adapted to a spectral analysis of a selected gas sample, where this measuring cell is designed and adapted to co-ordinate light beams emitted from a means generating IR light in a direction toward a means receiving IR light, by affording a plurality of reflections of the emitted light beams from a number of reflection surfaces or reflection points assigned to the inner cavity of the measuring cell, thereby allowing creating the length of a predetermined measuring distance in the inner cavity of the measuring cell, first of all from the means generating IR light to the means receiving IR light, and where the cavity of said measuring cell is adapted to be able to contain the gas sample intended for a spectroanalytical absorption measurement in an electronics including calculation circuit having appurtenant circuits, storage devices and requisite algorithms.

The inner cavity of the measuring cell and the volume thereof are limited by a first part, such as a bottom part, allocated to the measuring cell, in co-operation with a second part, such as an upper part, allocated to the measuring cell, and where the first part and/or the second part should be assigned recesses and/or seats.

Assigned recesses may then be adapted to a passage of light beams, generated by the means generating IR light, and to a passage of these light beams through the measuring cell and finally assigned a direction toward the means receiving IR light.

Assigned seats may then be adapted to be able to hold the means generating IR light and/or the means receiving IR light.

Generated light beams, from the means generating IR light, may then be directed and/or adapted to, such as reflectable, in a first reflection surface, in order to, by this reflection surface, become reflected and directed to a second reflection surface, here shaped as a concave reflection surface.

As for measuring cells, adapted to the above-mentioned technical field, it is previously known to allow forming these measuring cells as discrete components, with the means generating IR light structured as a first discrete unit, and attachable to a card having printed wiring, while the means receiving IR light is structured as a second discrete unit and attachable to a card having printed wiring. These two discrete units are then formed for electric co-operation with said card having printed wiring for co-operation with the requisite electronics and calculation circuit.

In such an arrangement, the proper measuring cell can be formed as a third discrete unit, where this unit is shaped into a tube having mirror faces related to the ends and which mirror faces let reflect light beams from a means (lamp) reflecting light and by the assigned longitudinally orientated axis thereof forming a right angle with a longitudinally orientated axis assigned to the tube.

It is also previously known to allow designing measuring cells that support the means generating light and the means receiving light and that form a discrete unit, structured for mechanical and electric co-operation with a card having printed wiring.

As examples of the above-mentioned prior art, furthermore the contents of the international patent publications WO 97/18 460-A1 and WO 98/09 152-A1 may be mentioned.

When considering the ray path in the inner cavity associated with the present invention reference should be made, as a further example of prior art, to the figures and contents of the international patent publication WO 2004/063725, where an embodiment is shown and described where a diverging light beam from a focal point is to be reflected in a concave reflection surface and against a plane reflection surface, in order to be reflected again against the concave reflection surface, in order to finally converge toward a means or detector receiving IR light laterally orientated to a focusing or focal point for the diverging light beam.

SUMMARY OF THE PRESENT INVENTION

Technical Problems

If attention is paid to the circumstance that the technical considerations that a person skilled in the relevant technical field has to do to be able to present a solution to one or more technical problems raised, are, on one hand, initially a necessary understanding of the measures and/or the sequence of measures that have to be taken, and on the other hand a necessary selection of the means that is/are required, then the subsequent technical problems would, in view of this, be relevant in the creation of the present subject matter of invention.

Considering prior art, such as it has been described above, it should, therefore, be seen as a technical problem to be capable of realizing the significance of, the advantages associated with and/or the technical measures and considerations that will be required in order to, in a measuring cell adaptable to a spectral analysis of a gas sample and having means for electric and mechanical co-operation with a carrier, such as a card having printed wiring, where said measuring cell is designed and adapted to, in the cavity of the measuring cell, allow co-ordinating light beams emitted from a means generating light in a direction toward a means receiving light, by allowing utilizing a plurality of reflections of said emitted light beams from a number of reflection surfaces (or reflection points) assigned to the inner cavity of the measuring cell, thereby allowing creating a predetermined, optical measuring distance in the inner cavity of the measuring cell, such as from the means generating light to the means receiving light, and where the cavity of said measuring cell is adapted to allow containing the gas sample intended for a spectroanalytical absorption measurement and where the inner cavity of the measuring cell and the volume thereof are limited by a first part, in the form of a bottom part, allocated to the measuring cell, in co-operation with a second part, such as an upper part, allocated to the measuring cell, and where the first part and/or the second part are/is assigned recesses and/or seats, where assigned recesses are adaptable to a passage of light beams, generated by the means generating light, and to a passage of light beams assigned a direction toward the means receiving light, while assigned seats are adaptable in order to entirely or partly be able to hold the means generating light and/or the means receiving light, besides which light beams, from the means generating light, are directed to and/or adaptable, such as reflectable, in a first reflection surface, in order to thus reflected become directed to a second reflection surface, shaped as a first concave reflection surface, allow creating conditions so that the measuring cell should be structurable within limited outer dimensions, with a limited number of reflection surfaces and reflection points, but still afford a measuring distance that is long enough for a reliable establishment of current measured values, in the intended spectroanalytical evaluation in the electronics.

There is a technical problem to be capable of realizing the significance of, the advantages associated with and/or the technical measures and considerations that will be required in order to allow the first part to be adapted to rest against said carrier, which, within its surface faceable to the carrier, is formed with one or two recesses or seats in order to entirely or partly allow surrounding, at least, said means generating light.

There is a technical problem to be capable of realizing the significance of, the advantages associated with and/or the technical measures and considerations that will be required in order to allow the carrier, within its surface faceable to the first part, to be formed with one or two recesses or seats in order to entirely or partly allow surrounding, at least, said means generating light.

There is a technical problem to be capable of realizing the significance of, the advantages associated with and/or the technical measures and considerations that will be required in order to allow the first reflection surface reflecting light to be adapted to allow directing light generated by the means to the cavity of the measuring cell and for a propagation within a first central plane, separated from a second central plane assigned to said means generating light and a longitudinally orientated axis assigned to the means.

There is a technical problem to be capable of realizing the significance of, the advantages associated with and/or the technical measures and considerations that will be required in order to, between the carrier and the second part, allow the first part to be arranged as an intermediate orientated part portion, which, together with the carrier, the first part and the second part, forms said first reflection surface preceding the second concave reflection surface.

There is a technical problem to be capable of realizing the significance of, the advantages associated with and/or the technical measures and considerations that will be required in order to allow the first part, or the intermediate orientated part portion, to be adapted to have a seat or a recess faceable to the carrier, adapted to allow surrounding one half, or essentially one half, of the means generating light.

There is a technical problem to be capable of realizing the significance of, the advantages associated with and/or the technical measures and considerations that will be required in order to allow the first part, or the intermediate orientated part portion, to be adapted to form a space faceable to the carrier, for the formation of a protected space or room for electronic components, such as electronic components related as discrete units and related to the card by a printed wiring.

There is a technical problem to be capable of realizing the significance of, the advantages associated with and/or the technical measures and considerations that will be required in order to, within the first part, or the intermediate orientated part portion, allow said means receiving light to be entirely or partly installed.

There is a technical problem to be capable of realizing the significance of, the advantages associated with and/or the technical measures and considerations that will be required in order to allow said first part, or its intermediate intermediate orientated part portion, together with the second part and the carrier, to form a common second concave reflection surface, in order to direct generated converging light beams, via reflection surfaces, to the means receiving light and the light detector thereof.

There is a technical problem to be capable of realizing the significance of, the advantages associated with and/or the technical measures and considerations that will be required in order to allow this second concavely curved reflection surface to be adapted to enclose said means generating light and, via said concave reflection surface, allow concentrating generated converging light beams to a deflecting first reflection surface, in order to, via a focusing point, be convergingly reflected toward the second, such as the first concavely shaped, reflection surface.

There is a technical problem to be capable of realizing the significance of, the advantages associated with and/or the technical measures and considerations that will be required in order to allow these light beams reflected from the second reflection surface to be convergingly directed to a third reflection surface, favourably shaped as a plane reflection surface.

There is a technical problem to be capable of realizing the significance of, the advantages associated with and/or the technical measures and considerations that will be required in order to allow these converging light beams reflected from the third reflection surface to be directed to a fourth reflection surface, favourably shaped as an essentially plane reflection surface.

There is a technical problem to be capable of realizing the significance of, the advantages associated with and/or the technical measures and considerations that will be required in order to allow these diverging light beams reflected from the fourth reflection surface to be directable again to the second reflection surface.

There is a technical problem to be capable of realizing the significance of, the advantages associated with and/or the technical measures and considerations that will be required in order to allow these light beams reflected again from the second reflection surface to be adaptable and directed, as converging light beams, to a reflection surface, orientated next to the means receiving light, upon the formation of a third focal point of the intended measuring distance.

There is a technical problem to be capable of realizing the significance of, the advantages associated with and/or the technical measures and considerations that will be required in order to allow these light beams, allocated for generated light, in the means generating light to be adapted to be reflected from a reflection surface converging light beams that should be orientated preceding the first plane reflection surface as counted in the direction of travel or propagation of the light beams.

There is a technical problem to be capable of realizing the significance of, the advantages associated with and/or the technical measures and considerations that will be required in order to allow a fifth reflection surface or reflection point to be adapted to direct the light beams reflected from the second reflection surface to the means receiving light.

There is a technical problem to be capable of realizing the significance of, the advantages associated with and/or the technical measures and considerations that will be required in order to allow the measuring cell to be adapted to have an inner cavity and a shape connecting to a parallelogram, in a section, or a parallelepiped, such as with right angles or at least essentially right angles, such as the shape of a rectangle in cross-section.

There is a technical problem to be capable of realizing the significance of, the advantages associated with and/or the technical measures and considerations that will be required in order to allow the second reflection surface to be adapted with a curvature in the cavity, such as a partly elliptic curvature, with a distance from the outer surface of the measuring cell to a curved wall portion of the cavity of the measuring cell varying from "0" to "2-4":10, as measured along a shorter side of the measuring cell and the cavity thereof.

There is a technical problem to be capable of realizing the significance of, the advantages associated with and/or the technical measures and considerations that will be required in order to allow the third reflection surface with its reflection point to be related to a longer side of the inner shape or cavity of the measuring cell.

There is a technical problem to be capable of realizing the significance of, the advantages associated with and/or the technical measures and considerations that will be required in order to allow the fourth reflection surface to be adapted to have a length of 25 to 40% of a shorter side allocated to the measuring cell.

There is a technical problem to be capable of realizing the significance of, the advantages associated with and/or the technical measures and considerations that will be required in order to allow the fourth reflection surface to be adapted to assume an oblique angle to said shorter side.

There is a technical problem to be capable of realizing the significance of, the advantages associated with and/or the technical measures and considerations that will be required in order to allow the fourth reflection surface to be adapted to receive incident IR light beams within a selected angle of incidence of an allocated central ray.

There is a technical problem to be capable of realizing the significance of, the advantages associated with and/or the technical measures and considerations that will be required in order to allow providing such a design of the measuring cell that the same will be able to have a selected ratio between "the length of the measuring distance/the outer volume of the measuring cell" that, using a millimeter rule, gives a ratio of 1:7 to 1:60 ($mm^{-2}$), such as between 1:10 to 1:30, say about 1:20.

There is a technical problem to be capable of realizing the significance of, the advantages associated with and/or the technical measures and considerations that will be required in order to allow the second part to contain the entire cavity, and there have a limited height dimension, such as from 1 to 5 mm, such as 2 to 4 mm.

There is a technical problem to be capable of realizing the significance of, the advantages associated with and/or the technical measures and considerations that will be required in order to allow the length of the measuring distance to be adapted to embrace two to four focal points, such as three focal points at a measuring distance of 100 mm or thereabout, where two focal points give a shorter measuring distance and four focal points give a longer measuring distance.

There is a technical problem to be capable of realizing the significance of, the advantages associated with and/or the technical measures and considerations that will be required in order to allow said cavity to be contained in, at least, two co-ordinated parts, in the form of plastic details, and having outer dimensions of approx. 20×25×2-4 mm or thereabout.

There is a technical problem to be capable of realizing the significance of, the advantages associated with and/or the technical measures and considerations that will be required in order to allow the means generating light to be adapted to have a frequency coverage falling within the infrared (IR) range.

The Solution

In that connection, the present invention starts out from the known technique provided by way of introduction and is based on a measuring cell adaptable to a spectral analysis of a gas sample and having means for electric and mechanical co-operation with a carrier, such as a card having printed wiring, where said measuring cell is designed and adapted to allow co-ordinating light beams emitted from a means generating light in a direction toward a means receiving light, by allowing utilizing a plurality of reflections of said emitted light beams from a number of reflection surfaces (or reflection points) assigned to the inner cavity of the measuring cell, thereby allowing creating a predetermined optical measuring distance in the inner cavity of the measuring cell, such as from the means generating light to the means receiving light, and where the cavity of said measuring cell is adapted to allow containing the gas sample intended for a spectroanalytical absorption measurement and where the inner cavity of the measuring cell and the volume thereof are limited by a first part, in the form of a bottom part, allocated to the measuring cell, in co-operation with a second part, such as an upper part, allocated to the measuring cell, and where the first part and/or the second part are/is assigned recesses and/or seats, where assigned recesses are adaptable to a passage of light beams, generated by the means generating light, and to a passage of light beams assigned a direction toward the means receiving light, while assigned seats are adaptable in order to entirely or partly be able to hold the means generating light and/or the means receiving light, besides which light beams, from the means generating light, are convergingly directed to and/or adaptable, such as reflectable, in a first reflection surface (or reflection point) in order to thus reflected become directed, via a first focal point, to a second reflection surface (or reflection point), shaped as a first concave reflection surface.

In order to be able to solve one or more of the above-mentioned technical problems, the present invention particularly teaches that the known technique should be supplemented in that the first part should be adapted to rest against said carrier, which, within its first surface faceable to the carrier, is formed with one or two recesses or seats, in order to entirely or partly allow surrounding, at least, said means generating light.

The carrier is, within its first surface faceable to the first part, formed with one or two recesses or seats, in order to entirely or partly allow surrounding, at least, said means generating light, and that the first reflection surface reflecting light is adapted to allow directing generated light to a first, an upper, plane, separated from a second, a lower, plane assigned to said means generating light and its longitudinally orientated axis.

Furthermore, it is taught that, between the carrier and the second part, the first part should be arranged, as an intermediate orientated part portion, and that forms, together with the carrier, the first part and the second part, said first reflection surface preceding a second, a first concavely shaped, reflection surface.

The first part, or the intermediate orientated part portion, should then be adapted to have a seat or a recess faceable to the carrier, adapted to allow surrounding one half, or essentially one half, of the means generating light.

The first part, or the intermediate orientated part portion, may be adapted to form a space faceable to the carrier, for the formation of a protected space for electronic components.

Furthermore, it is taught that, within the first part, or the intermediate orientated part portion, said means receiving light should be entirely or partly installed.

Said first part, or its intermediate orientated part portion, should, together with the second part, form a common, a second, concave reflection surface in order to direct generated light beams, via reflection surfaces and reflection points, to the means receiving light and the light detector thereof.

The second concavely curved reflection surface should be adapted to enclose said means generating light and, via said concave reflection surface, allow concentrating generated light beams to a deflecting first reflection surface, in order to, via a focusing point or focal point, be convergingly reflected toward the second, such as the first concavely shaped, reflection surface.

Furthermore, it is taught that these light beams reflected from the second reflection surface should be convergingly directed to a third reflection surface, shaped as a plane reflection surface, while these converging light beams reflected from the third reflection surface should be directed to a fourth reflection surface, shaped as a plane or essentially plane reflection surface, while these diverging light beams reflected from the fourth reflection surface again should be directable to the second reflection surface, and that these converging light beams reflected thereby from the second reflection surface are adapted and directed to the means receiving light.

In order to be able to solve one or more of the above-mentioned technical problems, the present invention in addition teaches that the thus known technique should be supplemented in that these light beams allocated as generated light in the means generating light should be adapted to be convergingly reflected from a reflection surface that should be preceding the first reflection surface as counted in the direction of travel or propagation of the light beams.

As proposed embodiments, falling within the scope of the fundamental idea of the present invention, moreover it is taught that a fifth (second) reflection surface should be adapted to allow directing these light beams reflected from the fourth reflection surface to the means receiving light.

In addition, it is taught that the measuring cell should be adapted to allow having an inner cavity and shape connecting to a parallelogram, in a section, or a parallelepiped, such as with right angles or at least essentially right angles, such as the shape of a rectangle in cross-section.

The second reflection surface should then be adapted with a curvature in the cavity, such as a partly elliptic (parabolic or cylindrical) curvature, with a distance from the outer surface of the measuring cell to a curved wall portion of the cavity of the measuring cell varying from "0" to "2-4":10, as measured along a shorter side of the cavity of the measuring cell.

The third reflection surface should then be related to a longer side of the inner shape or cavity of the measuring cell.

The fourth reflection surface should be adapted to have a length of 25 to 40% of a shorter side allocated to the measuring cell.

The fourth reflection surface should be adapted to assume an oblique angle to said shorter side.

The fourth reflection surface should be adapted to receive incident light beams within a selected angle of incidence of a central ray.

Furthermore, such a design of the measuring cell is taught that the same will be able to have a selected ratio between "the length of the measuring distance/the outer (inner) volume of the measuring cell" that, using a millimeter rule, will be able to give the ratio of 1:7 to 1:60 (mm$^{-2}$), such as between 1:10 to 1:30, say about 1:20 (mm$^{-2}$).

The second part should then contain the cavity and there have a height dimension from barely less than 1.0 mm to 5 mm, such as from 2 to 4 mm.

The length of the measuring distance may be adapted to embrace two to four focal points, such as three focal points at a measuring distance of 100 mm or thereabout, where two focal points give a shorter measuring distance and four focal points give a longer measuring distance with a corresponding change at the position and/or shape of the reflection surfaces as well as the placement of the means.

Said cavity should be contained in, at least, two co-ordinated parts, in the form of plastic details, and may then have outer dimensions of 20×25×2-4 mm or thereabout for an optical measuring distance of approx. 100 mm.

The means generating light should be adapted to have a frequency coverage within the infrared (IR) range.

Advantages

The advantages that foremost may be regarded as characteristic of the present invention and the special significative features provided thereby are that, in this way, conditions have been created in order to, in a measuring cell adapted to a spectral analysis of a gas sample, according to the preamble to the following claim 1, allow teaching that a first part should be adapted to rest against a carrier, which, within its first surface faceable to the carrier, is formed with one or two recesses or seats and adapted to allow surrounding one half of or the entire, at least, said means generating light.

The carrier should, within its first surface faceable to the first part, be formed with one or two recesses or seats, adapted in order to entirely or partly allow surrounding, at least, said means generating light.

What foremost can be regarded as characteristic of the present invention is defined in the characterizing clause of the subsequent claim 1.

BRIEF DESCRIPTION OF THE DRAWINGS

A presently proposed embodiment, having the significative features associated with the present invention, will now for the purpose of exemplifying be described more in detail, reference being made to the accompanying drawing, wherein.

DESCRIPTION OF A PRESENTLY PROPOSED EMBODIMENT

It should then by way of introduction be emphasized that in the subsequent description of a presently proposed embodiment, which has the significative features associated with the invention and which is elucidated by the figures shown in the appended drawings, we have selected terms and a particular terminology with the intention to thereby primarily allow making evident the proper inventive idea.

It should, however, in this connection be taken into consideration that expressions selected here should not be seen as limiting solely to the terms utilized and selected here, but it should be understood that each term selected in this manner should be interpreted so that it, in addition, will be able to embrace all technical equivalents operating in the same or substantially the same way, in order to, in this way, enable the achievement of the same or substantially the same intention and/or technical effect.

Thus, with a reference to the appended FIGS. 1 to 8, the fundamental conditions of the present invention are shown schematically and in detail, and where the significative features associated with the invention have been made concrete, by the presently proposed embodiment described more in detail in the following.

Figure 1:
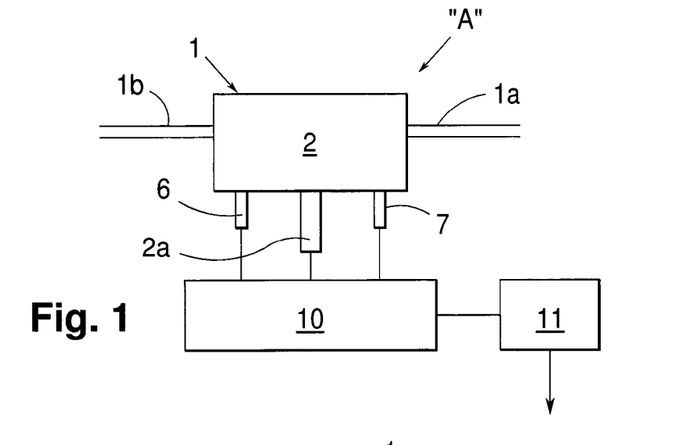
FIG. 1 shows in a simplified illustration a gas sensor having a measuring cell or a gas cell, in accordance with the features of the present invention, as well as schematically the electronics required to evaluate a frequency-dependent light intensity within a selected spectral range, in order to afford a spectroanalytical evaluation in the electronics and the calculation unit thereof, as well as present it on a display (not shown)

Accordingly, FIG. 1 shows, in a simplified representation, a gas sensor "A" and that embraces a measuring cell or gas cell 1 as well as the requisite electronics 10, in order to, by means of the same, allow evaluating a frequency-dependent light intensity in the spectroanalytical arrangement 11, in the form of a calculation unit or calculation circuit.

The electronics 10 is adapted to allow evaluating the frequency-dependent light intensity in a light beam or light rays that pass through openings 6 and 7 as well as allow comparing the result of a frequency-dependent light intensity from a source of light 2a and, depending on occurring discrepancy, allow analysing the gas or the gas mixture, contained in a cavity 2 of the measuring cell 1, but also evaluating the concentration of the gas or gas mixture, which can pass through lines 1a and 1b.

The principal structure of these gas sensors "A" is previously known and will therefore not be described in detail.

Figure 2:
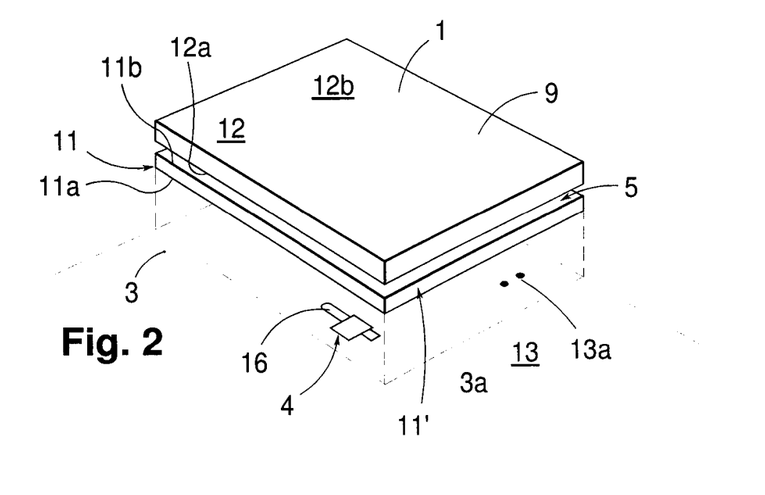
FIG. 2 shows in a perspective representation a measuring cell with its two parts, according to the features of the invention, placed, for the purpose of clarification, somewhat above a carrier, in the form of a card having printed wiring, a printed board or a printed board assembly.

The present invention concerns basically a new design or the measuring cell 1, which in FIG. 2 is illustrated with its two parts 11, 12, somewhat above a carrier 13 or a card 3 for printed wiring, but that should co-operate with the upper surface 3a of the card and that is shown with a means 4 generating light and a means 5 receiving light, placed as discrete components at the upper surface 3a of the card or entirely or partly be configured in the card 3 and/or the measuring cell 1 and its second part 12.

Figure 3:
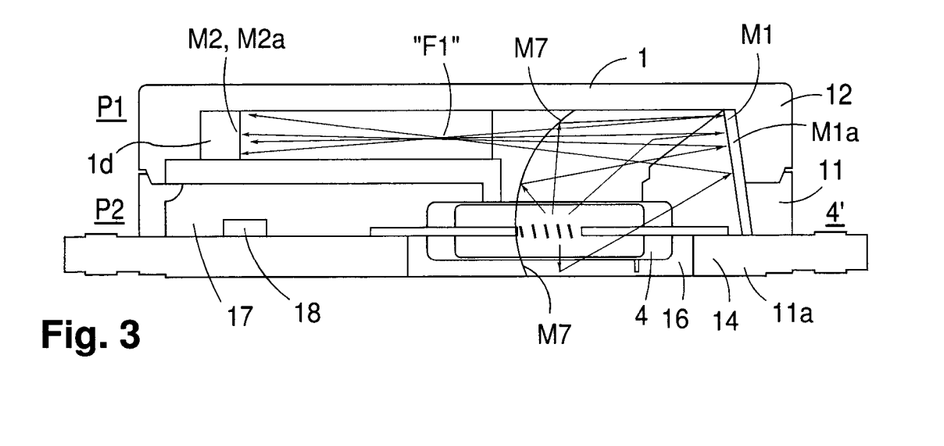
FIG. 3 shows in a section the measuring cell placed on said card in order to illustrate a ray path from a means generating light toward and to a first reflection surface in order to be reflected against a first concave reflection surface, formed as a second reflection surface.
Figure 4:
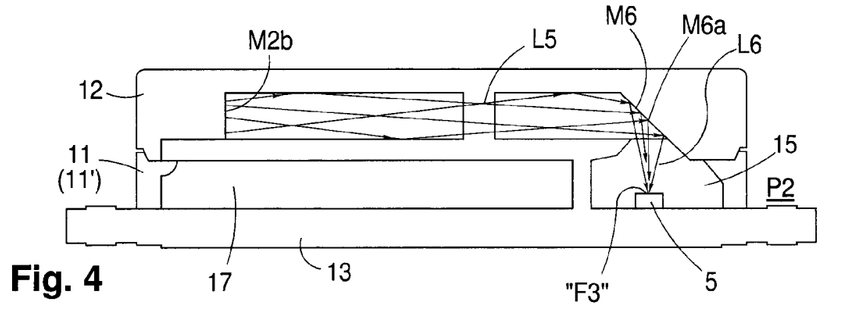
FIG. 4 shows in a section the measuring cell placed on said card in order to illustrate a ray path from the second reflection surface, or the first concave reflection surface, toward and to a light-receiving means.

Then, FIGS. 3 and 4 illustrate in more detail in side view the design of the measuring cell 1, where the first part 11 is in co-operation with the second part 12 and with a carrier 13, in the form of a printed board or printed board assembly 3.

With reference, foremost to FIGS. 2 to 8, it is illustrated that the present invention basically relates to a measuring cell 1 adaptable to a spectral analysis of a gas sample, having means 13a for an electric (and mechanical) co-operation with the carrier 13, such as a card 3 having printed wiring.

Said measuring cell 1 is designed and adapted to allow co-ordinating light beams emitted from the means 4 generating light in a direction toward a means 5 receiving light, by allowing utilizing a plurality of reflections of said emitted light beams from a number of reflection surfaces (or simplified reflection points of a central ray) assigned to the inner cavity 1c of the measuring cell 1.

Here, the reflection surfaces have been assigned the reference designations M1, M2, M3, etc., for a first, a second, a third reflection surface, etc., having the reference designations M1a, M2a, etc., for assigned reflection points.

Thereby, the reflection surfaces (with their reflection points) are adapted to allow creating a predetermined, optical measuring distance "L" in the inner cavity 1c of the measuring cell, such as from the means 4 generating light to the means 5 receiving light.

The inner cavity 1c of said measuring cell 1 is adapted to allow containing the gas sample "G" intended for a spectroanalytical absorption measurement and inlet and outlet for the gas sample may be formed by formed ducts next to the means 4.

The inner cavity 1c of the measuring cell and its volume are limited by a first part 11, in the form of a bottom part, allocated to the measuring cell and the other surface 11b thereof, in co-operation with a second part 12, such as an upper part, allocated to the measuring cell and one surface 12a thereof.

The first part 11 and/or the second part 12 are/is assigned recesses 14, 15 and/or seats, where assigned recesses in that connection are adaptable to a passage of light beams, generated by the means 4 generating light, and to a passage of light beams assigned a direction toward the means 5 receiving light.

Assigned seats may then be adaptable in order to entirely or partly be able to hold the means 4 generating light and/or the means 5 receiving light, as discrete components.

Figure 7:
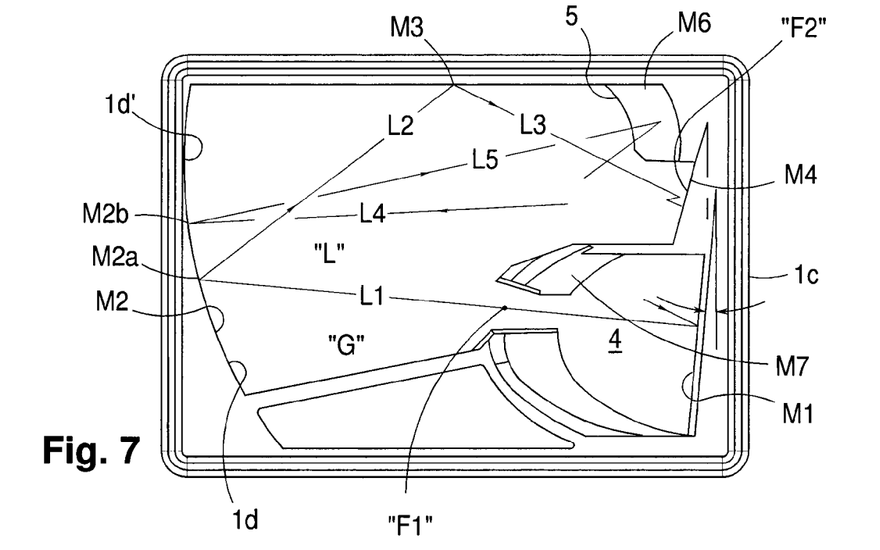
FIG. 7 shows the measuring cell according to FIG. 5 with the light beams, diverging and converging, for the formation of a first and a second focal point.

Light beams, from the means 4 generating light and via a (second) concavely shaped reflection surface M7, are convergingly directed to and/or adaptable, such as reflectable, in a first reflection surface M1, in order to thus reflected, via a first focal point "F1" become divergingly directed to a second reflection surface M2, shaped as a first concave reflection surface (see FIG. 7).

The first part 11 is adapted to rest against said carrier 13, which, within its first surface 11a faceable to the carrier 13, is formed with one or two recesses 14, 17 or seats in order to entirely or partly allow surrounding, at least, said means 4 generating light.

The carrier 13 is, within its first surface 3a faceable to the first part 11, formed with one or two recesses 16 or seats in order to entirely or partly allow surrounding, at least, said means 4 generating light.

FIG. 3 teaches that the first reflection surface M1 reflecting light is adapted to be to allow directing generated converging light to a first plane "P1", separated from a second plane "P2" assigned to said means 4 generating light and its longitudinally orientated (horizontal) axis 4'.

Between the carrier 13 and the second part 12, the first part 11 is arranged as an intermediate orientated part portion 11'.

Said part portion 11' forms, together with the carrier 13, the first part 11 and the second part 12, said first plane reflection surface M1 preceding the second concavely shaped reflection surface, designated M7.

The first part 11, or the intermediate orientated part portion 11', is adapted to have, according to FIG. 3, a seat or a recess 14 facing the carrier 13 and its first surface 3a for the half, or essentially the half, means 4 generating light.

The first part 11, or the intermediate orientated part portion, is adapted to form a space 17 faceable to the carrier 13 and its first surface 3a for the formation of a space, here designated 18, intended for electronic components and protected by the first part 11.

With reference to FIG. 4, it is illustrated that, within the first part 11, or the intermediate orientated part portion, said means 5 receiving light is installed in order to, via electric connectors 13a, be co-ordinatable with electronics 18 belonging to a printed circuit card.

The second concavely curved reflection surface M7 is adapted to enclose said means 4 generating light and, via said concave reflection surface M7, allow concentrating generated light beams to a deflecting first plane reflection surface M1 in order to, via a first focusing point or focal point "F1" in the plane P1, be reflected against the second, such as the first concavely shaped, reflection surface M2.

Figure 5:
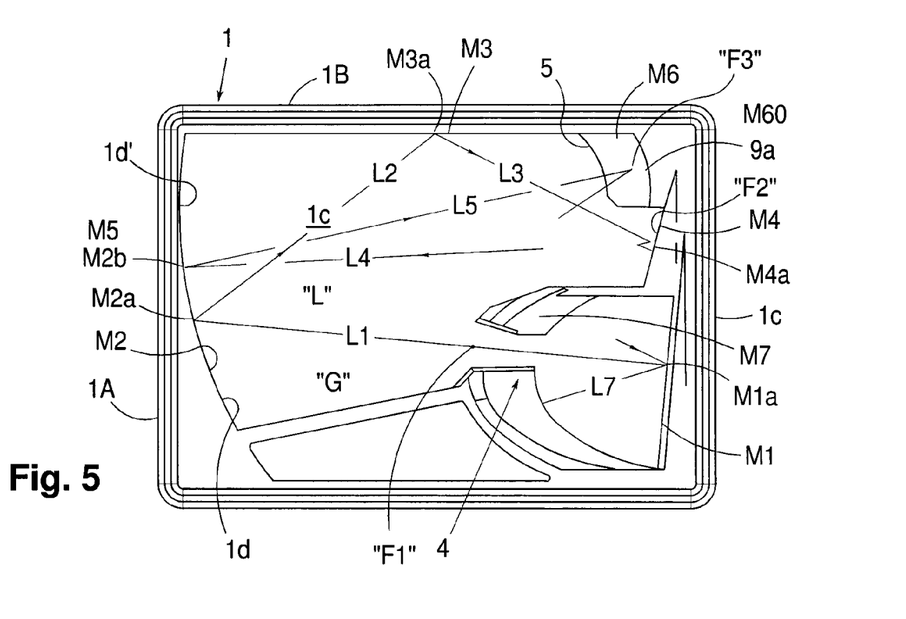
FIG. 5 shows in a planar view the construction of the measuring cell with recesses and reflection surfaces within the second part of the measuring cell, as well as with a proposed central ray-related light or ray path for generated light in the form of light beams and with indicated reflection points in formed reflection surfaces.
Figure 6:
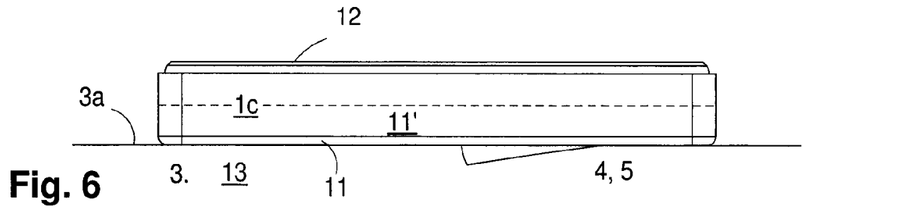
FIG. 6 shows the measuring cell in a side view, resting against a schematically formed printed board.

Then, FIG. 5 illustrates in more detail the measuring cell 1 and its inner structure in the cavity 1c thereof including its reflecting surfaces or indicated reflection points M1a, M2a, M3a, M4a, M2b and M6, with the focal point "F3" where these reflection points indicate the point of impact of a virtual central ray.

Figure 8:
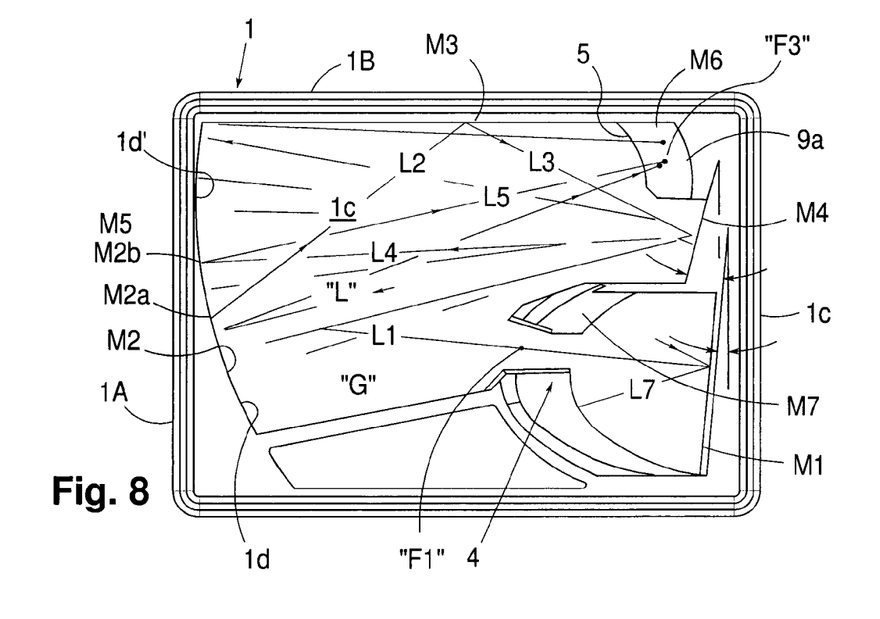
FIG. 8 shows the measuring cell, according to FIG. 5, with the light beams diverging from the second focal point and converging toward a third focal point.

In order to allow illustrating a selected central ray path, from the means 4 generating light to the means 5 receiving light, this has in FIG. 5 been illustrated by single lines L1, L2, L3, L4 and L5 allocated to central rays, between the reflection points M1a-M6a ("F3"), but it should be taken into consideration that the proper ray path has a wider dispersion, such as diverging or converging, than the one illustrated and that is elucidated in FIGS. 7 and 8.

Light beams from the means 4 generating light are, via a concave reflection surface M7, convergingly directed to and/ or adapted, such as reflectable, in the first plane reflection surface M1, in order to when reflected become directed, as L1, to the second reflection surface M2 and its reflection point M2a, shaped as a first concave reflection surface, via a first focal point "F1".

The light beams L2 reflected from the second reflection surface M2 are directed to a third reflection surface M3, here shaped as a plane reflection surface, while the light beams L3 reflected from the third reflection surface M3 are directed to a fourth reflection surface M4, shaped as a plane, or somewhat concavely curved reflection surface in order to in the same, or in the vicinity thereof, form a second focal point "F2".

The light beams L4 reflected from the fourth reflection surface M4 become, according to FIG. 8, again directed to the second reflection surface M2 and there illustrated as a reflection point M2b, and that the light beams L5 reflected from the second reflection surface M2 and the reflection point M2b, via the reflector surface M6, are adapted and directed, as concentrated light beams L6, to the means 5 receiving light in order to there occur as a third focal point "F3".

The light beams allocated to the generated light in the means 4 generating light are adapted to be reflected from a reflection surface M7 immediately preceding the first reflection surface M1 as counted in the direction of travel or propagation of the light beams.

A fifth reflection point M2*b* in the second reflection surface M2 is adapted to allow directing the converging light beams L5 reflected by the reflection surface M4 to the means 5 receiving light, via an inclined reflection surface M6, in order to form the third focal point "F3".

The measuring cell 1 is adapted to allow having an inner cavity 1*c* and shape connecting to a parallelogram, in a section, or a parallelepiped, such as with right angles or at least essentially right angles, such as the shape of a rectangle in cross-section.

The angle of incidence of the light beams M7 to the first reflection surface M1 is, as for the central ray "L7" thereof, selected to be less than 15°, such as between 5° and 10°.

The second reflection surface M2 is adapted with a curvature in the cavity 1*c*, such as a partly elliptic curvature 1*d'*, with a distance from the outer surface 1A of the measuring cell 1 to a curved wall portion 1*d* of the cavity of the measuring cell varying from "0" to "2-4":10 along a shorter side 1A of the measuring cell 1.

The third reflection surface M3 is related to a longer side 1B of the inner shape or cavity 1*c* of the measuring cell 1 and is here shaped plane, but could be somewhat curved.

The fourth reflection surface M4 is adapted to have a length of 25 to 40% of a shorter side 1C allocated to the measuring cell and somewhat angled for allowing the light pulses to concentrate to the detector 5 as a third focal point "F3".

The fourth reflection surface M4 is adapted to assume an angle to a shorter side 1C of 10° to 20°, such as about 15°. Here, the sides 1A and 1C are parallel.

The fourth reflection surface M4 is furthermore adapted to receive incident light beams L3 within an angle of incidence of 15° to 30°, such as about 20°.

Said cavity 1*c* is contained in, at least, two co-ordinated parts 11, 12, in the form of plastic details, and has, in a preferred embodiment, outer dimensions of 20×25×2-6 mm or thereabout, for allowing forming an optical measuring distance of approx. 100 mm.

The cavity 1*c* is mainly built-in within the second part 12, one surface of which 12*a* is open in order to connect to the upper plane surface of the first part 11, designated its other surface 11*b*.

Furthermore, it is suggested that the means 4 generating light should be adapted to have a frequency or a frequency coverage within the infrared (IR) range.

Here, the reflection surface M7 is shaped as a part of a revolution ellipsoidal or revolution paraboloidal reflection surface, with the lighting point of the source of light 4 orientated in or next to its foci.

The possibility of allowing forming the reflection surfaces plane or curved, depending on the requirement of received and/or reflected light beams, falls within the scope of the invention.

With reference to FIGS. 3, 4 and 5, it is seen that the light beam generated by the means 4 becomes, by the reflection surface M7, converging toward the first focal point "F1" and diverging toward the reflection surface M2, in order to be convergingly directed, via the reflection point M2*a*, to the reflection surface M3 and to the reflection surface M4 and there form a second focal point "F2" in order to after that form a diverging light beam toward the reflection surface M2 and its second reflection point M2*b* in order to from there form a converging light beam toward the reflection surface M6, for the formation of a third focal point "F3" in the detector 5.

The invention affords different shapes of utilized reflection surfaces, where the reflection surfaces M7 and M2 should be convex but where the other surfaces may be plane or somewhat curved, in order to collect the light beams toward the focal point "F3", which should be situated in or near the detector 5.

Furthermore, such a design of the measuring cell is taught that the same will be able to have a selected ratio between "the length of the measuring distance/the outer (inner) volume of the measuring cell" that, using a millimeter rule, gives a ratio of 1:7 to 1:60 ($mm^{-2}$), such as between 1:10 to 1:30, say about 1:20 ($mm^{-2}$).

The second part 12 should then contain the cavity 1*c* and there have a height dimension from 1 to 5 mm, such as 2 to 4 mm.

The length of the measuring distance may be adapted to embrace two to four focal points, such as three focal points at a measuring distance of 100 mm or thereabout, where two focal points give a shorter measuring distance and four focal points give a longer measuring distance.

The invention is of course not limited to the embodiment given above as example, but may be subjected to modifications within the scope of the general idea according to the invention, illustrated in the subsequent claims.

Particularly, it should be taken into consideration that each unit and/or category shown can be combined with any other unit and/or category shown within the scope in order to be able to attain the desired technical function.

The invention claimed is:

1. A measuring cell for spectro-analytical absorption measurement and spectral analysis of a gas sample contained in said measuring cell and for electric and mechanical co-operation with a carrier, said measuring cell comprising:
    a means for generating light,
    a means for receiving light,
    an inner cavity comprising a number of reflection surfaces thus defining a predetermined, optical measuring path length in the inner cavity of the measuring cell, whereby the inner cavity of the measuring cell is defined by a first part and a second part which co-operate with each other, and
    whereby the first part and/or the second part comprise respective recesses and/or seats, whereby the recesses allow a passage of light beams respectively from the means for generating light and to the means for receiving light,
    whereby the seats entirely or partly hold the means for generating light and/or the means for receiving light,
    whereby the number of reflection surfaces comprises a first reflection surface and a second reflection surface having a concave shape, the first reflection surface reflecting light to the second reflection surface,
    whereby the first part is adapted to rest against said carrier with a first surface facing the carrier being formed with one or two recesses or seats, in order to entirely or partly surround at least said means for generating light, and
    whereby the first reflection surface light is adapted to direct light generated by the means for generating light to a first plane, separated from a second plane in which said means for generating light is located, and that the first part forms a space facing the carrier for the formation of a protected space for electronic components.

2. The measuring cell according to claim 1, wherein between the carrier and the second part, the first part is arranged as an intermediate orientated part portion, which forms, together with the carrier, the first part and the second part, said first reflection surface preceded by an additional concave reflection surface.

3. The measuring cell according to claim 2, wherein, within the first part, or the intermediate orientated part portion, said means for receiving light is installed.

4. The measuring cell according to claim 2, wherein the additional concave reflection surface is adapted to enclose said means for generating light and, via said additional concave reflection surface, allow concentrating generated light beams to the first reflection surface in order to, via a first focusing point, be reflected against the second reflection surface.

5. The measuring cell according to claim 1, wherein the first part, or an intermediate orientated part portion, is adapted to have a seat or a recess facing the carrier, adaptable to one half, or essentially one half, of the means for generating light.

6. The measuring cell according to claim 1, wherein, said first part, or its intermediate orientated part portion, forms, together with the second part and the carrier, a common concave reflection surface, in order to convergingly allow directing generated light beams, via the number of reflection surfaces and focal points, to the means for receiving light and a light detector thereof.

7. The measuring cell according to claim 1, wherein converging light beams reflected from the second reflection surface are, as converging light beams, directed to a third reflection surface, shaped as a plane reflection surface, that converging light beams reflected from the third reflection surface are directed to a fourth reflection surface, that light beams reflected from the fourth reflection surface are, via a second focal point, directed to the second reflection surface, and that converging light beams reflected thereby from the second reflection surface are directly or indirectly adapted and directed to the means for receiving light, as a third focal point.

8. The measuring cell according to claim 7, wherein a fifth reflection surface or reflection point, in the second reflection surface, is adapted to allow directing the light beams reflected from the fourth reflection surface to the means for receiving light.

9. The measuring cell according to claim 7, wherein the third plane reflection surface is related to a longer side of the inner cavity of the measuring cell.

10. The measuring cell according to claim 7, wherein the fourth reflection surface is adapted to have a length of 25 to 40% of a shorter side allocated to the measuring cell.

11. The measuring cell according to claim 10, wherein the fourth reflection surface is adapted, as for a central ray, to assume an angle to said shorter side of 10° to 20°.

12. The measuring cell according to claim 7, wherein the fourth reflection surface is adapted to receive, as for a central ray, incident light beams within an angle of incidence of 15° to 30°.

13. The measuring cell according to claim 1, wherein light beams allocated to the generated light in the means for generating light are adapted to be reflected from a part of a revolution ellipsoidal or revolution paraboloidal reflection surface preceding the first reflection surface as counted in the direction of travel or propagation of the light beams.

14. The measuring cell according to claim 1, wherein the inner cavity anti has a shape of a parallelogram, in section, or a parallelepiped.

15. The measuring cell according to claim 1, wherein the angles of incidence of the light beams, as for a central ray, to the first reflection surface are selected to be less than 10°.

16. The measuring cell according to claim 1, wherein the second reflection surface is adapted with a curvature in the inner cavity, with a distance from the outer surface of the measuring cell to a curved wall portion of the inner cavity of the measuring cell varying from "0" to 2-4:10 along a shorter side of the inner cavity of the measuring cell.

17. The measuring cell according to claim 1, wherein said inner cavity is contained in, at least, two co-ordinated parts, in the form of plastic details, and having outer dimensions of approximately 20×25×2-4 mm, for an optical measuring distance of approximately 100 mm.

18. The measuring cell according to claim 1, wherein the means for generating light is adapted to have a frequency coverage within the infrared (IR) range.

19. The measuring cell according to claim 1, wherein design of the measuring cell is adapted to be able to have a selected ratio between the length of the measuring distance and the inner volume of the measuring cell that, using a millimeter rule, gives a ratio of 1:7 to 1:60 ($mm^{-2}$).

20. The measuring cell according to claim 1, wherein the second part accommodates the inner cavity having a height dimension from 1 to 5 mm.

21. The measuring cell according to claim 1, wherein the length of the measuring distance is adapted to embrace two to four focal points, where two focal points give a shorter measuring distance and four focal points give a longer measuring distance.

22. The measuring cell according to claim 1, wherein the means for generating light is a lamp with its a longitudinally orientated axis related to, or in close connection to, a plane of the upper surface of the carrier, in order to reduce the requisite structure height.

* * * * *